US008935628B2

(12) United States Patent
Chernilo

(10) Patent No.: US 8,935,628 B2
(45) Date of Patent: Jan. 13, 2015

(54) USER INTERFACE FOR MEDICAL DIAGNOSIS

(76) Inventor: Jonathan Chernilo, Queensland (AU)

( * ) Notice: Subject to any disclaimer, the term of this patent is extended or adjusted under 35 U.S.C. 154(b) by 483 days.

(21) Appl. No.: 13/106,829

(22) Filed: May 12, 2011

(65) Prior Publication Data

US 2012/0290957 A1    Nov. 15, 2012

(51) Int. Cl.
*G06F 3/048*    (2013.01)
*G06F 19/00*    (2011.01)

(52) U.S. Cl.
CPC ........ *G06F 19/3406* (2013.01); *A61M 2205/52* (2013.01); *Y10S 715/968* (2013.01)
USPC ............................ 715/781; 715/764; 715/968

(58) Field of Classification Search
CPC ................................................ A61M 2205/52
USPC .................. 715/968, 764; 345/419; 382/276; 378/62
See application file for complete search history.

(56) References Cited

U.S. PATENT DOCUMENTS

| | | | | |
|---|---|---|---|---|
| 6,032,678 A * | 3/2000 | Rottem | .......................... | 600/437 |
| 6,792,071 B2 * | 9/2004 | Dewaele | .......................... | 378/62 |
| 6,964,639 B2 * | 11/2005 | Sela et al. | ..................... | 600/443 |
| 7,065,235 B2 * | 6/2006 | Dewaele | .......................... | 382/132 |
| 7,394,946 B2 * | 7/2008 | Dewaele | .......................... | 382/276 |
| 7,799,077 B2 * | 9/2010 | Lang et al. | ................. | 623/14.12 |
| 7,979,383 B2 * | 7/2011 | Heilbrunn et al. | ............ | 707/792 |
| 8,083,745 B2 * | 12/2011 | Lang et al. | ...................... | 606/87 |
| 8,105,330 B2 * | 1/2012 | Fitz et al. | ......................... | 606/88 |
| 8,126,234 B1 * | 2/2012 | Edwards et al. | .............. | 382/128 |
| 8,306,960 B2 * | 11/2012 | Kakimoto et al. | ............ | 707/705 |
| 8,337,501 B2 * | 12/2012 | Fitz et al. | ..................... | 606/86 R |
| 8,337,507 B2 * | 12/2012 | Lang et al. | ..................... | 606/102 |
| 8,343,218 B2 * | 1/2013 | Lang et al. | ................. | 623/16.11 |
| 8,401,259 B2 * | 3/2013 | Matsue et al. | ................ | 382/128 |
| 2002/0082866 A1 * | 6/2002 | Ladouceur et al. | .............. | 705/2 |
| 2003/0053673 A1 * | 3/2003 | Dewaele | ....................... | 382/132 |
| 2003/0194057 A1 * | 10/2003 | Dewaele | ....................... | 378/210 |
| 2004/0171924 A1 | 9/2004 | Mire et al. | | |
| 2005/0154302 A1 * | 7/2005 | Sela et al. | ..................... | 600/443 |
| 2006/0277073 A1 * | 12/2006 | Heilbrunn et al. | ................ | 705/3 |
| 2007/0179626 A1 | 8/2007 | De La Barrera et al. | | |
| 2007/0198022 A1 * | 8/2007 | Lang et al. | ..................... | 606/88 |
| 2009/0226068 A1 * | 9/2009 | Fitz et al. | ...................... | 382/131 |
| 2009/0276045 A1 * | 11/2009 | Lang | ......................... | 623/14.12 |

(Continued)

OTHER PUBLICATIONS

Steinberg et al., "Preoperative planning of total hip replacement using the TraumaCad™ system", Archives of Orthopaedic and Trauma Surgery, vol. 130, issue 12, Jan. 13, 2010, pp. 1429-1432.

(Continued)

*Primary Examiner* — William Titcomb
(74) *Attorney, Agent, or Firm* — Greenberg Traurig, LLP

(57) ABSTRACT

A user interface 10, configured to be installed in a computing apparatus, for medical diagnosis, includes a display arrangement for displaying an image 28 of a part of a patient's body on a display device of the apparatus, the image 28 including an abnormality associated with that part of the patient's body. A library of representations 52-58 is accessible by a user, the representations 52-58 depicting abnormalities associated with that part of the body, at least some of the representations 52-58 being able to be displayed on the display arrangement. A selection means is operable by the user for selecting one of the representations and for overlying the selected representation 52-58 on the image 28 to enable the user to identify the abnormality.

45 Claims, 16 Drawing Sheets

(56) References Cited

U.S. PATENT DOCUMENTS

| | | | |
|---|---|---|---|
| 2010/0131294 A1 | 5/2010 | Venon et al. | |
| 2010/0153081 A1* | 6/2010 | Bellettre et al. | 703/11 |
| 2010/0179428 A1* | 7/2010 | Pedersen et al. | 600/443 |
| 2010/0272085 A1* | 10/2010 | Baier | 370/338 |
| 2010/0305973 A1 | 12/2010 | McLaren et al. | |
| 2011/0071581 A1 | 3/2011 | Lang et al. | |
| 2011/0071802 A1* | 3/2011 | Bojarski et al. | 703/1 |
| 2011/0077499 A1* | 3/2011 | Pagani, IV | 600/407 |
| 2011/0082711 A1 | 4/2011 | Poeze et al. | |
| 2011/0301982 A1* | 12/2011 | Green et al. | 705/3 |
| 2012/0008848 A1* | 1/2012 | Beck | 382/132 |
| 2012/0194505 A1* | 8/2012 | Beck | 345/419 |

OTHER PUBLICATIONS

Michalikova et al., "The digital pre-operative planning of total hip replacements", Applied Machine Intelligence and Informatics (SAMI), 2010 IEEE 8$^{th}$ International Symposium on Applied Machine Intelligence and Informatics, Jan. 29-30, 2010, pp. 279-282.

Patent Examination Report No. 1, issued on Jan. 2, 2014 by the Australian Government IP Australia for Patent Application No. 2011202211.

* cited by examiner

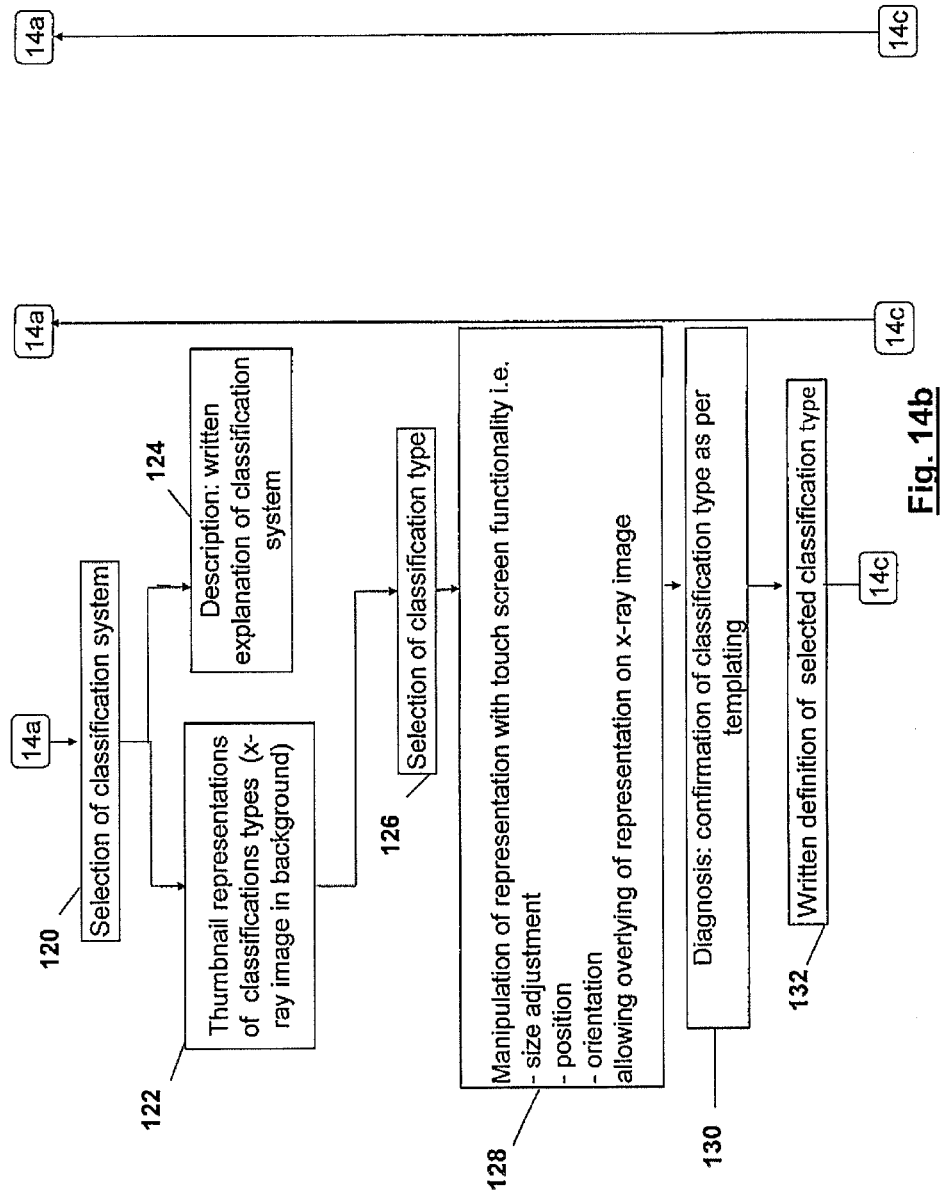

USER INTERFACE FOR MEDICAL DIAGNOSIS

BACKGROUND

Field

This disclosure relates, generally, to medical diagnosis of abnormalities and, more particularly, to a user interface for medical diagnosis, to a computer readable medium having a computer executable medical diagnosis application and a computer implemented method executable on a general purpose computing apparatus and to a handheld device including the user interface.

SUMMARY

In one aspect, there is provided a user interface, configured to be installed in a computing apparatus, for medical diagnosis, the user interface including:

a display arrangement for displaying an image of a part of a patient's body on a display device of the apparatus, the image including an abnormality associated with that part of the patient's body;

a library of representations which is accessible by a user, the representations depicting abnormalities associated with that part of the body, at least some of the representations being able to be displayed on the display arrangement; and a selection means operable by the user for selecting one of the representations and for overlying the selected representation on the image to enable the user to identify the abnormality.

The abnormality may be a fracture, an injury, an aneurysm, a blockage of a blood vessel, or the like. The disclosure has particular applicability to classifying fractures. Thus, in this specification the term "identify", and related terms, is to be understood in a broad sense to include classifying medical conditions such as fractures, sprains, ligament damage, dislocations, or the like. Those skilled in the art will, however, appreciate that the user interface can be used for diagnosing any medical condition which is based on visualisation of an abnormality which is able to be compared with a representation of that abnormality obtained from a database or which is able to be identified automatically using techniques such as pattern recognition technology.

In an embodiment, the user interface may be configured to use an image capture device of the apparatus for capturing the image of the part of the patient's body to be displayed on the display device. In another embodiment, the user interface may be configured to use a memory module of the apparatus for storing data relating to the image, the data being able to be retrieved on command from the memory module to display the image on the display device.

The user interface may include manipulation functionality for enabling the user to manipulate the selected representation to assist in identifying the abnormality. The manipulation functionality may comprise touch responsiveness of the display device of the apparatus to facilitate carrying out of operations by the user. The operations in question may be the selection of the representation, the manipulation of the representation (including rotation of the representation, enlarging or reducing the size of the representation on the screen, shifting the position of the representation, etc.), selecting other options, or the like. The operations may further include adjusting the colour and/or transparency of the representation using functionality of the apparatus as per the preference of the user and to assist in identification of the abnormality.

The operations which are able to be carried out by the user may include entering notes relating to the abnormality, accessing reference works relating to the identification of the abnormality or accessing literature relating to the abnormality and/or the treatment of such abnormality. The reference works and literature may be subscriber-based requiring the user to be a subscriber to be able to gain access to the reference works.

One of the operations which is able to be carried out by the user may include accessing information relating to medical devices to be used in treating the identified abnormality. The user interface may be configured to use geographical location determining functionality of the apparatus to enable the user to locate at least one vendor of the medical devices in, or in the vicinity of, a geographical area in which the user is located. The apparatus may have a geographical positioning system (GPS) associated with it and the user interface may make use of the GPS of the apparatus for locating the vendor. The user interface may also make use of the GPS of the apparatus to give information about medical devices available for that abnormality and which are located in the geographical area in which the apparatus is located.

The computing apparatus may be a mobile apparatus. The mobile apparatus may be a mobile telephone, a personal digital assistant, a portable computer including a tablet computer, or the like.

In a second aspect, there is provided a user interface, configured to be installed in a computing apparatus, for medical diagnosis, the user interface including:

a display arrangement for displaying an image of a part of a patient's body on a display device of the apparatus, the image including an abnormality associated with that part of the patient's body;

a library of representations which is accessible by a user, the representations depicting abnormalities associated with that part of the body, at least some of the representations being able to be displayed on the display device;

a selection means operable by the user for selecting one of the representations and for overlying the selected representation on the image to enable the user to identify the abnormality; and an accessing means for accessing a database containing information relating to medical devices available for treating the abnormality.

The user interface may be configured, using the accessing means, to cooperate with geographical location determining functionality of the apparatus to enable the user to locate at least one vendor of the medical devices in, or in the vicinity of, a geographical area in which the user is located.

In a third aspect, there is provided a computer readable medium having a computer executable medical diagnosis application executable on a general purpose computing apparatus, the medical diagnosis application including:

a medical data input module configured to receive data relating to an image of a part of a patient's body, the image including an abnormality associated with that part of the patient's body, the medical data input module further being configured to manipulate the data to enable the image to be displayed on a display device of the computing apparatus;

a data access module for accessing a library of representations depicting abnormalities associated with that part of the body and for displaying at least some of the representations on the display device of the computing apparatus; and a selection module responsive to an input from a user of the computing apparatus to select one of the representations and overlying the selected representation on the image to enable the user to identify the abnormality.

In an embodiment, the medical data input module may include an image processing module for processing the data relating to the image for displaying the image on the display device of the computing apparatus. In another embodiment, the medical data input module may include a memory access module for accessing stored data relating to the image, the data being able to be retrieved on command from the memory module to display the image on the display device.

The display device of the computing apparatus may be touch enabled and the computer readable medium may includes manipulation functionality responsive to touch inputs from the user for facilitating manipulation of the selected representation relative to the image displayed on the display device to assist in identifying the abnormality, the manipulation of the selected representation comprising at least one of repositioning the selected representation, resizing the selected representation and rotating the selected representation. The manipulation functionality may further be configured to facilitate carrying out of operations by the user on the computing apparatus.

The operations which are able to be carried out by the user may include at least one of entering notes relating to the abnormality, accessing reference works relating to the identification of the abnormality and accessing literature relating to the abnormality and/or the treatment of such abnormality.

The data access module may be configured to access information relating to medical devices to be used in treating the identified abnormality.

The computing apparatus may include geographical location determining functionality to identify a geographical area in which the computing apparatus is located and in which the data access module is configured to locate at least one vendor of the medical devices in, or in the vicinity of, the geographical area of the computing apparatus. The data access module may also be configured to use the functionality of the apparatus to give information about medical devices available for that abnormality and which are located in the geographical area in which the apparatus is located.

The computing apparatus may be a mobile apparatus.

In a fourth aspect there is provided a computer readable medium having a computer executable medical diagnosis application executable on a general purpose computing apparatus, the medical diagnosis application including:

a medical data input module configured to receive data relating to an image of a part of a patient's body, the image including an abnormality associated with that part of the patient's body, the medical data input module further being configured to manipulate the data to enable the image to be displayed on a display device of the computing apparatus;

a data access module for accessing a library of representations depicting abnormalities associated with that part of the body and for displaying at least some of the representations on the display device of the computing apparatus; and a selection module responsive to an input from a user of the computing apparatus to select one of the representations and overlying the selected representation on the image to enable the user to identify the abnormality;

wherein the data access module is further configured to access a database containing information relating to medical devices available for treating the abnormality.

The computing apparatus may include functionality to identify a geographical area in which the computing apparatus is located and the data access module may be configured to locate at least one vendor of the medical devices in, or in the vicinity of, the geographical area of the computing apparatus. The data access module may also be configured to use the functionality of the apparatus to give information about medical devices available for that abnormality and which are located in the geographical area in which the apparatus is located.

In a fifth aspect there is provided a computer implemented method for medical diagnosis to be executed on a general purpose computing apparatus, the method including:

receiving data relating to an image of a part of a patient's body, the image including an abnormality associated with that part of the patient's body and manipulating the data to enable the image to be displayed on a display device of the computing apparatus;

accessing a library of representations depicting abnormalities associated with that part of the body and displaying at least some of the representations on the display device of the computing apparatus; and selecting one of the representations and overlying the selected representation on the image to enable the user to identify the abnormality.

In an embodiment, the method may include processing the data relating to the image for displaying the image on the display device of the computing apparatus. In another embodiment, the method may include accessing stored data relating to the image, the data being able to be retrieved on command from the memory module to display the image on the display device.

The display device of the computing apparatus may be touch enabled and includes manipulation functionality responsive to touch inputs from the user and the method may include using the manipulation functionality to manipulate the selected representation relative to the image displayed on the display device to assist in identifying the abnormality, the manipulation of the selected representation comprising at least one of repositioning the selected representation, resizing the selected representation and rotating the selected representation.

The method may include using the manipulation functionality to carry out operations by the user on the computing apparatus, the operations to be carried out by the user including at least one of entering notes relating to the abnormality, accessing reference works relating to the identification of the abnormality, and accessing literature relating to the abnormality and/or the treatment of such abnormality.

The method may include accessing information relating to medical devices to be used in treating the identified abnormality. The method may include identifying a geographical area in which the computing apparatus is located and locating at least one vendor of the medical devices in, or in the vicinity of, the geographical area of the computing apparatus. The method may further include giving information about medical devices available for that abnormality and which are located in the geographical area in which the apparatus is located.

In a sixth aspect, there is provided a computer implemented method for medical diagnosis to be executed on a general purpose computing apparatus, the method including:

receiving data relating to an image of a part of a patient's body, the image including an abnormality associated with that part of the patient's body and manipulating the data to enable the image to be displayed on a display device of the computing apparatus;

accessing a library of representations depicting abnormalities associated with that part of the body and displaying at least some of the representations on the display device of the computing apparatus;

selecting one of the representations and overlying the selected representation on the image to enable the user to identify the abnormality; and accessing a database containing information relating to medical devices available for treating the abnormality.

The method may include identifying a geographical area in which the computing apparatus is located and locating at least one vendor of the medical devices in, or in the vicinity of, the geographical area of the computing apparatus. The method may further include giving information about medical devices available for that abnormality and which are located in the geographical area in which the apparatus is located.

The disclosure extends to a handheld device including a user interface as described above.

The handheld device may be a mobile device. Examples of mobile devices incorporating the user interface include mobile telephones commonly referred to as "smart phones", tablet computers, personal digital assistants (PDAs), or the like.

The user interface may be generated from a computer executable medical diagnosis application carried by a computer readable medium as described above.

BRIEF DESCRIPTION OF DRAWINGS

An embodiment of the disclosure is now described by way of example only with reference to the accompanying drawings in which:

FIG. 11 shows a screenshot of the user interface showing an example of information related to that abnormality obtained by clicking on another one of the displayed links in the screenshot of FIG. 9;

FIGS. 14a-14c show a flowchart of an embodiment of the computer executable medical diagnosis application.

DETAILED DESCRIPTION OF EXEMPLARY EMBODIMENT

Figure 1:
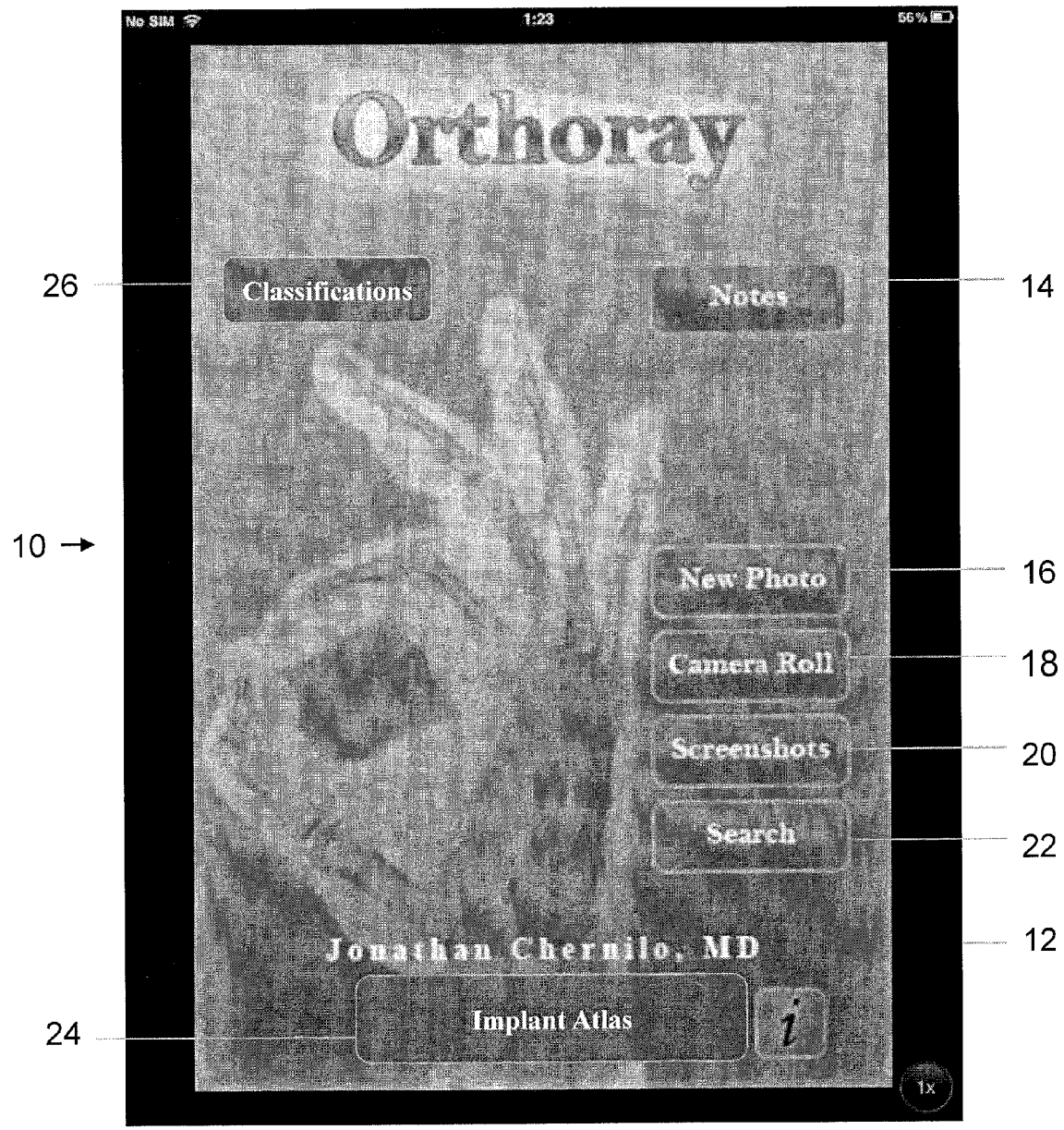
FIG. 1 shows a screenshot of a home screen of an embodiment of a user interface for medical diagnosis.

In the drawings, reference numeral 10 generally designates an embodiment of a user interface for medical diagnosis. The user interface 10 is contained in a general computing apparatus, more particularly, a mobile device. Examples of the mobile device include, but are not limited to, mobile telephones, particularly those referred to as "smart phones", portable computing devices such as tablet computers, netbook or notebook computers, personal digital assistance (PDAs), or the like. While the user interface 10 has been developed specifically for use with such mobile devices, it will be appreciated that the user interface 10, and its underlying computer application, could be used on any suitably configured general computing apparatus. It is therefore not intended to be limited to use only on handheld or mobile devices.

The user interface 10 is intended for use in diagnosing abnormalities associated with a patient's body. While the user interface 10 has been developed specifically for diagnosing and dealing with abnormalities in the form of fractures in a patient's body, it will be appreciated that the user interface 10 is able to be used, with little, if any, modification to diagnose other conditions such as the presence of strains or sprains, ligament damage, or the like. In addition, the user interface 10 is also able to be used with reference to other medical conditions such as the treatment of aneurysms, narrowing of blood vessels due to plaque build up, other blood vessel abnormalities such as wall thinning, or the like.

With particular reference to FIG. 1 of the drawings, an initial screenshot or home screen of the user interface 10 is illustrated. The home screen, designated generally by reference numeral 12, is displayed on a display of the device (not shown) containing the user interface 10.

The home screen 12 displays a plurality of fields. The fields which are displayed on the home screen include a Notes field 14, a New Photo field 16, a Camera Roll" field 18, a Screenshots field 20, a Search field 22, an Implant Atlas field 24 and a Classifications field 26. The user interface 10 makes use of a touch enabled display of the device. Thus, by a user touching the display in region overlying the required field, that field is activated.

The New Photo field 16 is operated by the user of the user interface 10 when it is desired to take a photo of an X-ray image 28 (FIG. 4) which is to be used in identifying and/or classifying a fracture contained in the X-ray image 28. The New Photo field 16 is operated by the user when the user wishes to use a camera (not shown) of the device containing the user interface 10.

Hence, when the user wishes to take a photograph of the X-ray image 28, the user touches the new photo field 16 which causes the image to be captured by the device and stored in a memory of the device.

If the X-ray image 28 has previously been photographed, it is stored in a memory of the device containing the user interface 10. The user can access this previously stored image by means of the Camera Roll field 18. In addition, the memory of the device also stores images which have been loaded into the device by other methods, for example, by being attachments to an email, multimedia message service (MMS), or the like.

The user uses the Camera Roll field 18 to access any one of such previously stored images.

In addition, if the X-ray image 28 is being displayed on the display of the device then, by using appropriate functionality of the device, the screenshot displayed can be saved by using the Screenshot field 20.

The Search field 22, as its name suggests, enables the user to search either the device or other resources for material which is of interest to the user.

The Implant Atlas field 24 enables the user to obtain details of companies which produce medical devices for use in the treatment of various fractures and, if desired orthopaedic pathology in general, as will be described in greater detail below.

Fractures are classified by various classification systems. Part of the purpose of the user interface 10 is to enable the user to classify a fracture contained in an X-ray image such as that depicted at 28 in FIG. 4 of the drawings using the relevant classification system. By activating the Classifications field 26, the user can obtain details regarding the various classification systems available.

Figure 2:
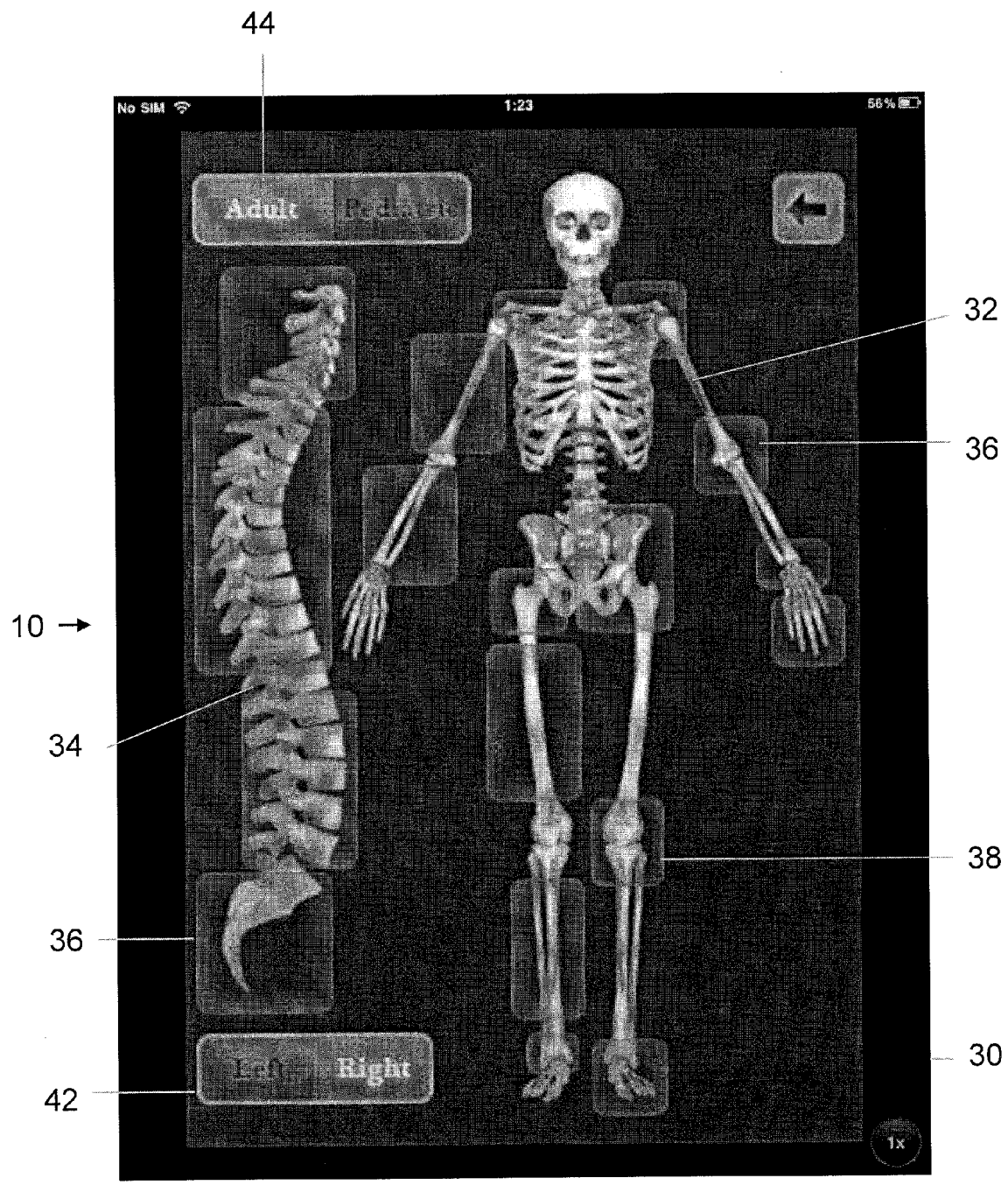
FIG. 2 shows a screenshot of the user interface showing a skeletal system with selectable segments.

Once an X-ray image 28 has been captured by the device containing the user interface 10, a second screen is displayed on the display of the device as shown by the screenshot 30 in FIG. 2 of the drawings. The screen contains a skeleton 32 as well as a part 34 of the skeleton 32 of a patient.

While the user interface 10 will generally be used in the treatment of human patients, those skilled in the art will appreciate that there is nothing preventing the user interface 10 being used in the treatment of other animal patients as well. It is intended by the applicant that the user interface 10 can be used for the treatment of other animals as well.

The skeletal image 32 and the part 34 have segments 36 which are highlighted. The user selects the relevant segment 36 by touching that part of the display overlying the relevant segment. In this case, the user selects segment 38 of the skeletal image 32 displayed on the screen of the device. The user can also select a Left/Right field 42 displayed in the screenshot 30 depending on which part of the skeleton is of interest. The user can indicate whether the patient is an adult or a child (paediatric) patient by means of a field 44 in the screenshot 30.

Figure 3:
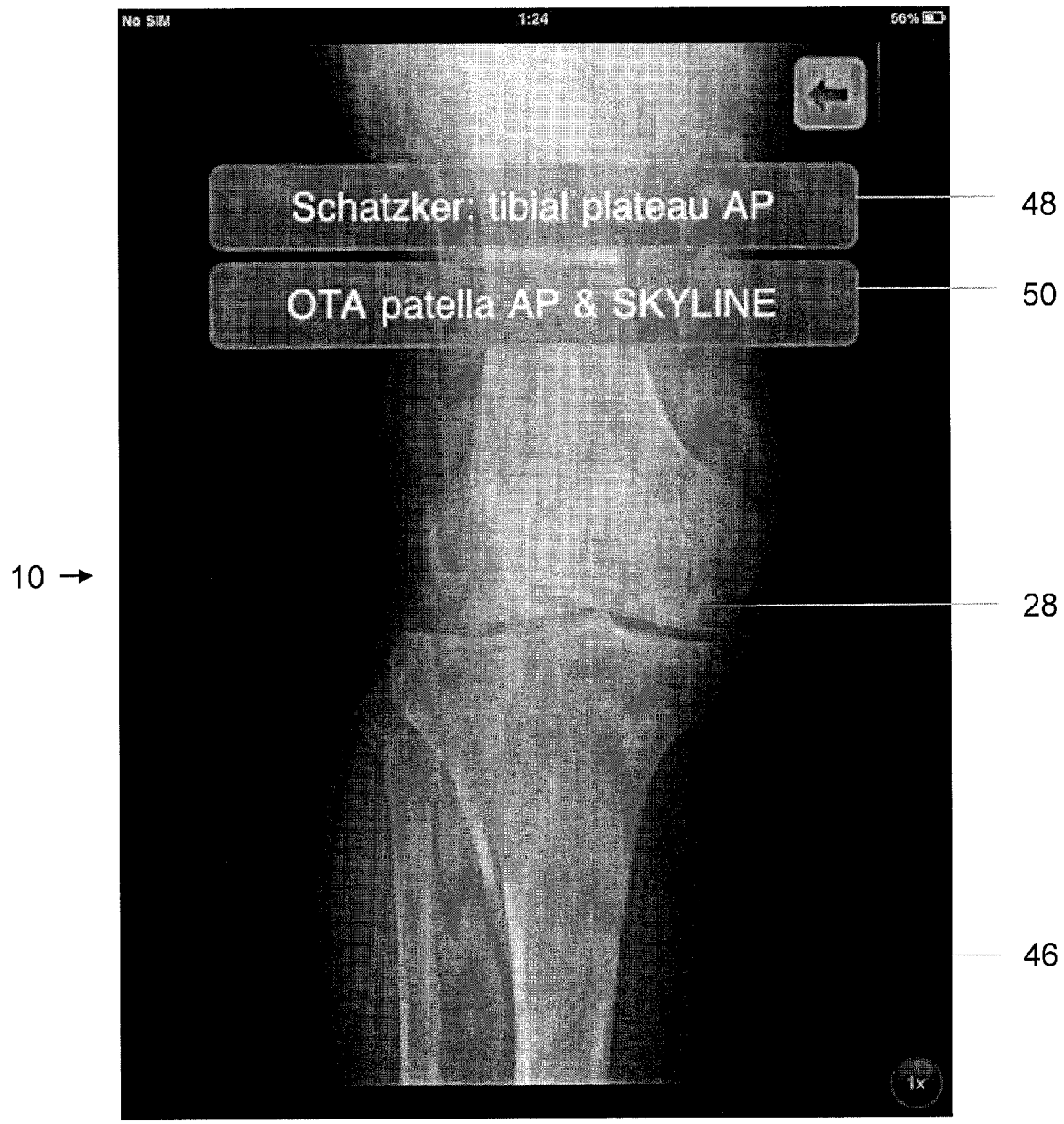
FIG. 3 shows a screenshot of the user interface showing an image of a part of a patient's body and selectable classification systems relating to identifying abnormalities associated with that part of the patient's body.

After the skeletal segment 38 and the relevant fields 42 and 44 have been selected, a further screen is displayed on the display of the device as illustrated by the screenshot 46 in FIG. 3 of the drawings. This screenshot 46 displays the X-ray image 28 as well fields 48 and 50 relating classification systems. While two classification systems 48 and 50 are illustrated, it will be appreciated that, in practice, a greater or fewer number of classification systems could be displayed in the screenshot 46.

Figure 4:
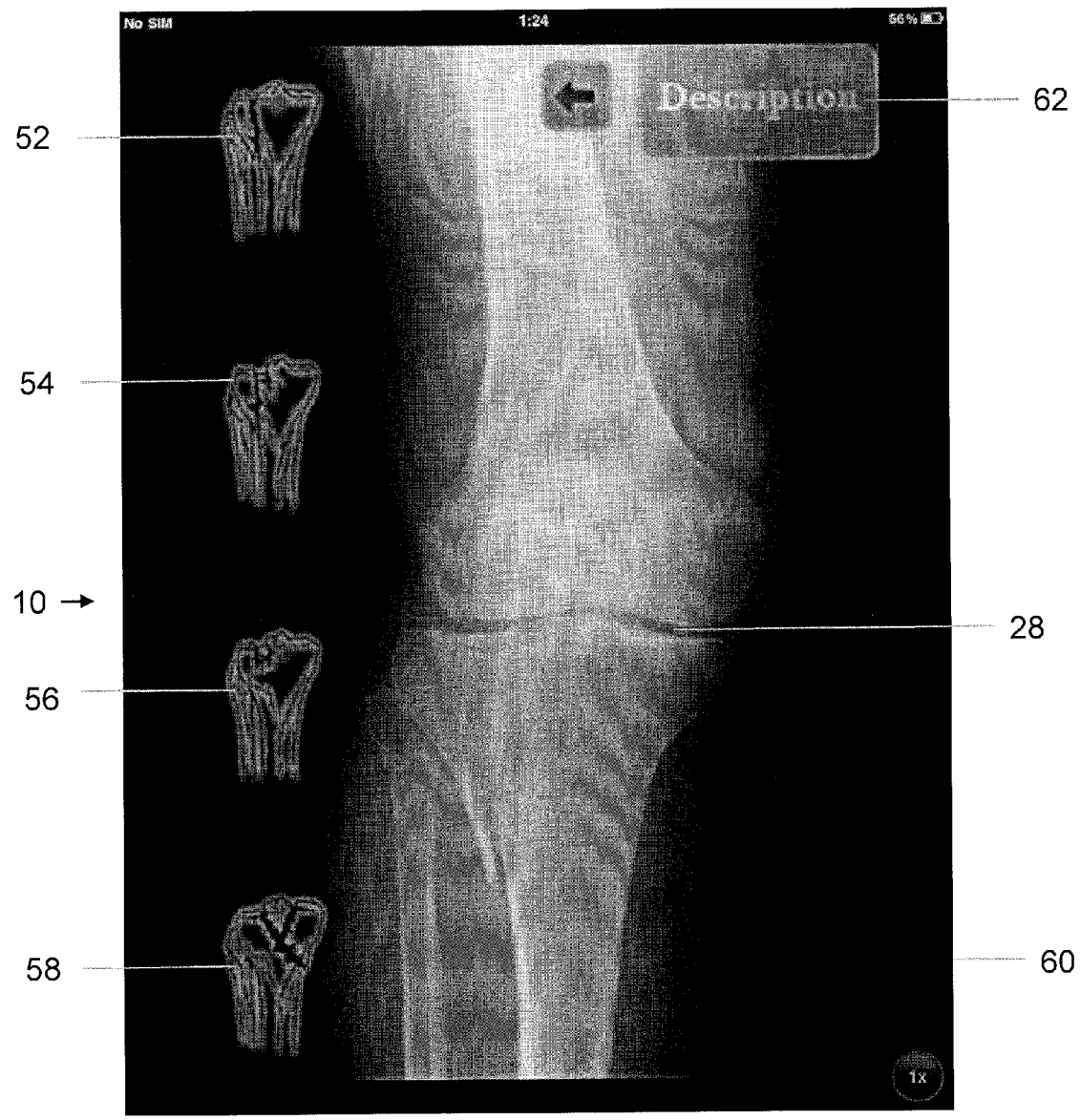
FIG. 4 shows a screenshot of the user interface showing a plurality of representations obtained from the selected classification system.

In this case, the user selects the field 48 to obtain the relevant classification. When this occurs, a further screen is displayed as shown in the screenshot 60 (FIG. 4). Together with the X-ray image 28, various representations in the form of illustrations 52, 54, 56 and 58 are displayed. The user can select the relevant illustration 52-58 which most closely approximates the fracture depicted in the X-ray image 28. A Description field 62 is also displayed in the screenshot 60 to enable the user to obtain a description of the classification system being used and/or the fracture in question.

Figure 5:
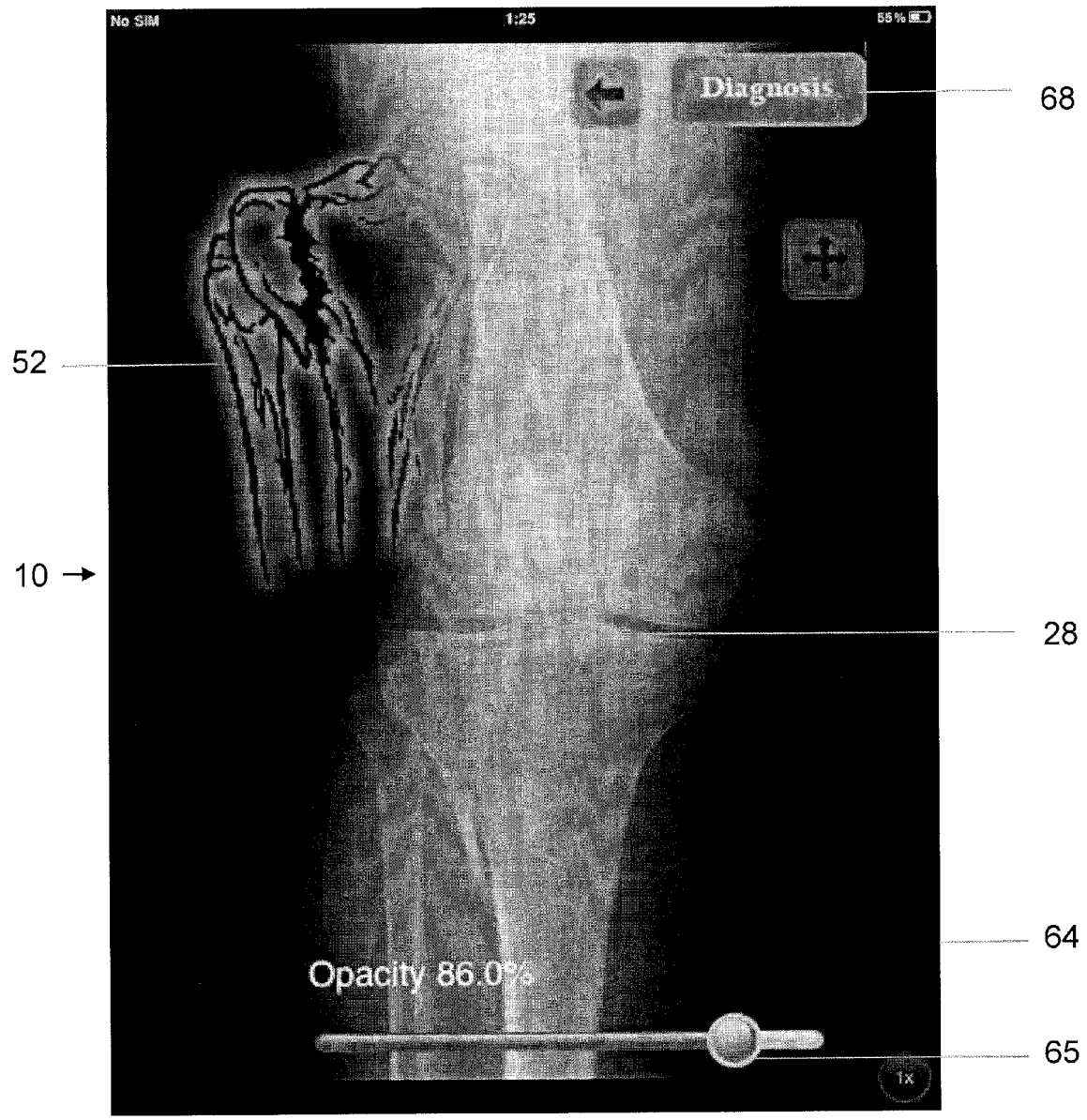
FIG. 5 shows a screenshot of the user interface showing a selected representation in the process of being manipulated on a display relative to the underlying image.
Figure 6:
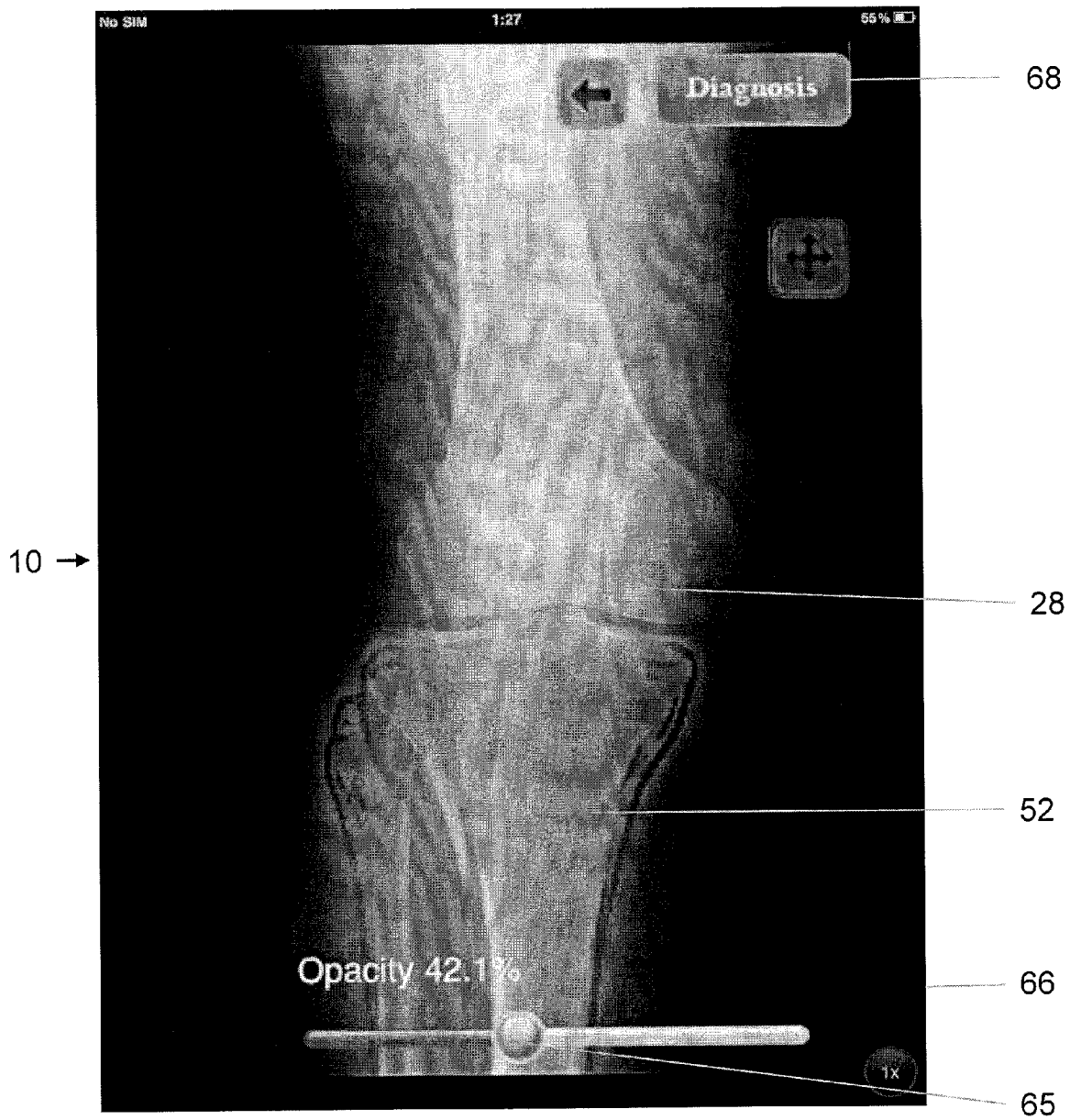
FIG. 6 shows a screenshot of the user interface after the selected representation has been positioned relative to the underlying image.

In the case of the X-ray image 28 depicted, the illustration which most closely approximates the fracture is that shown by illustration 52. Hence, as shown in a screenshot 64 in FIG. 5 of the drawings, the user selects the image 52. Using the touch screen functionality of the device, the user is able to manipulate the selected illustration 52. More particularly, the user can resize, reposition and rotate the selected illustration 52. The user manipulates the illustration 52 so that it overlies the fracture in the X-ray image 28 to enable the user to determine which type of fracture is present in the X-ray image 28. The user can also adjust the colour and/or transparency of the illustration 52 using functionality 65 of the apparatus as per the preference of the user and to assist in identification of the fracture. Once the illustration 52 overlies the X-ray image such as shown in a screenshot 66 of the display shown in FIG. 6 of the drawings, the user can activate a Diagnosis field 68. This can be done either in the screen of screenshot 64 or the screen of screenshot 66.

Figure 7:
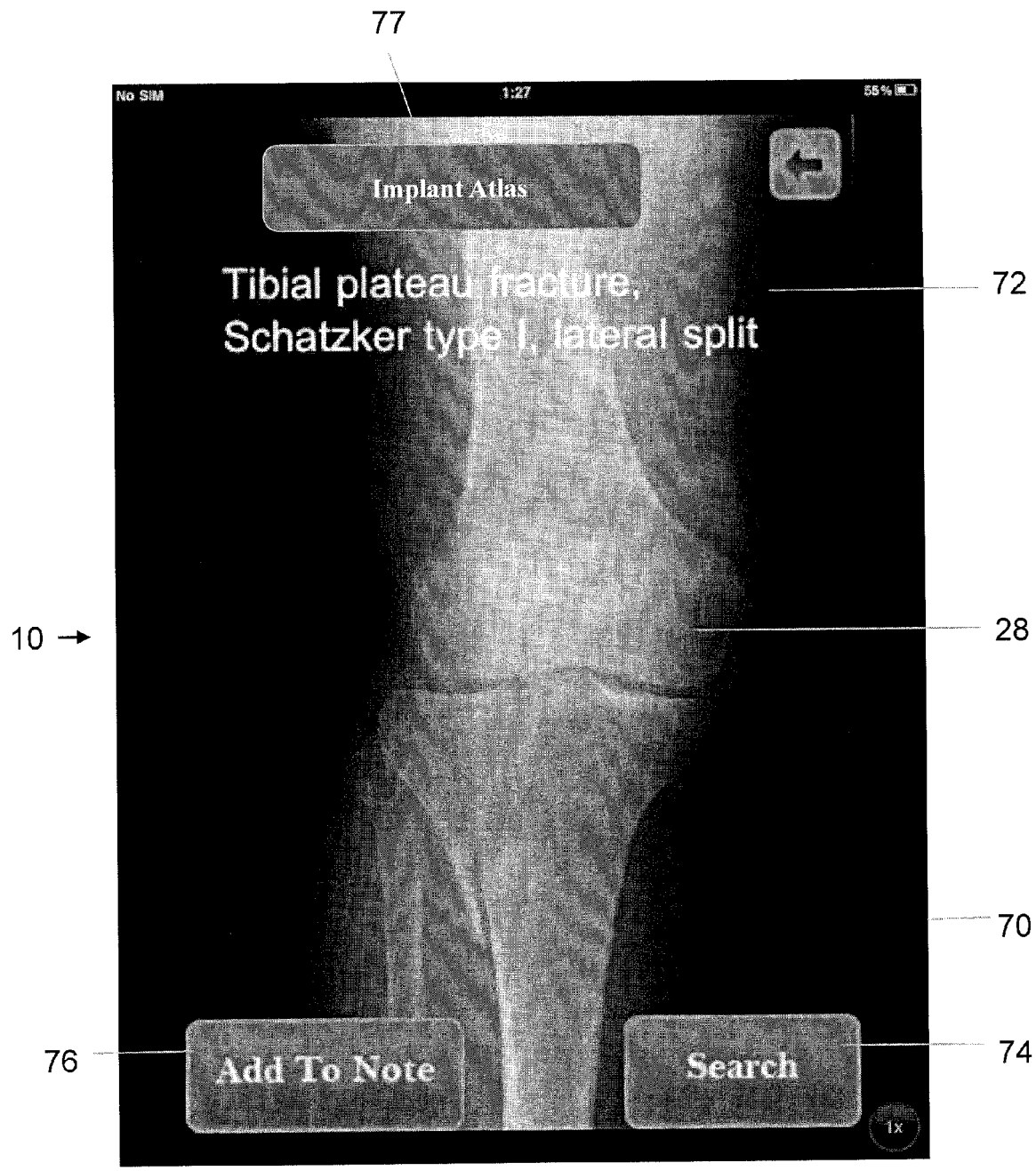
FIG. 7 shows a screenshot of the user interface identifying the abnormality as shown in the image using the selected representation.

When the user activates the Diagnosis field 68, a following screen is displayed, a screenshot of which is shown at 70 in FIG. 7 of the drawings. As illustrated in the screenshot 70, an identification of the fracture is displayed at 72. In addition, a Search field 74, an Add To Note field 76 and a further Implant Atlas field 77 are displayed. The fields 74, 76 and 77 correspond with the fields 22, 14, and 24 respectively of the screen illustrated in the screenshot 12 in FIG. 1 of the drawings.

Figure 8:
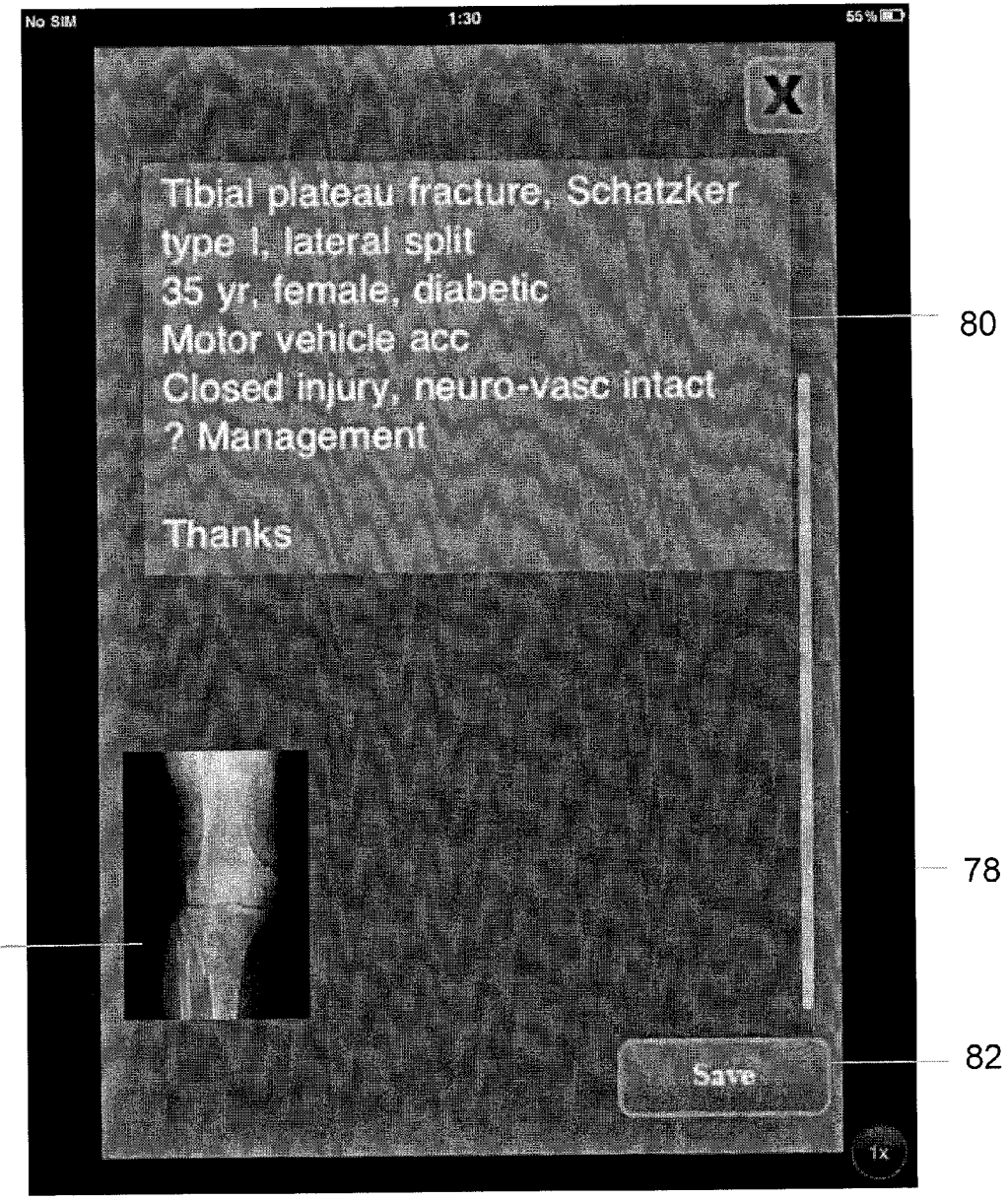
FIG. 8 shows a screenshot of the user interface showing notes relating to the identified abnormality made by a user of the interface.

The field 76 enables the user such as a clinician to enter notes relating to the patient and the fracture in question. FIG. 8 illustrates a screenshot 78 of the screen that is displayed after the user activates the field 76. The screen includes a window 80 and a reduced image of the X-ray 28. The user is able to enter details regarding the fracture and the patient in the window 80 and to save it using a Save field 82. The user can also transfer such information (details and picture or pictures) to a colleague for an opinion or for a referral, through e-mail, MMS, or the like.

Figure 9:
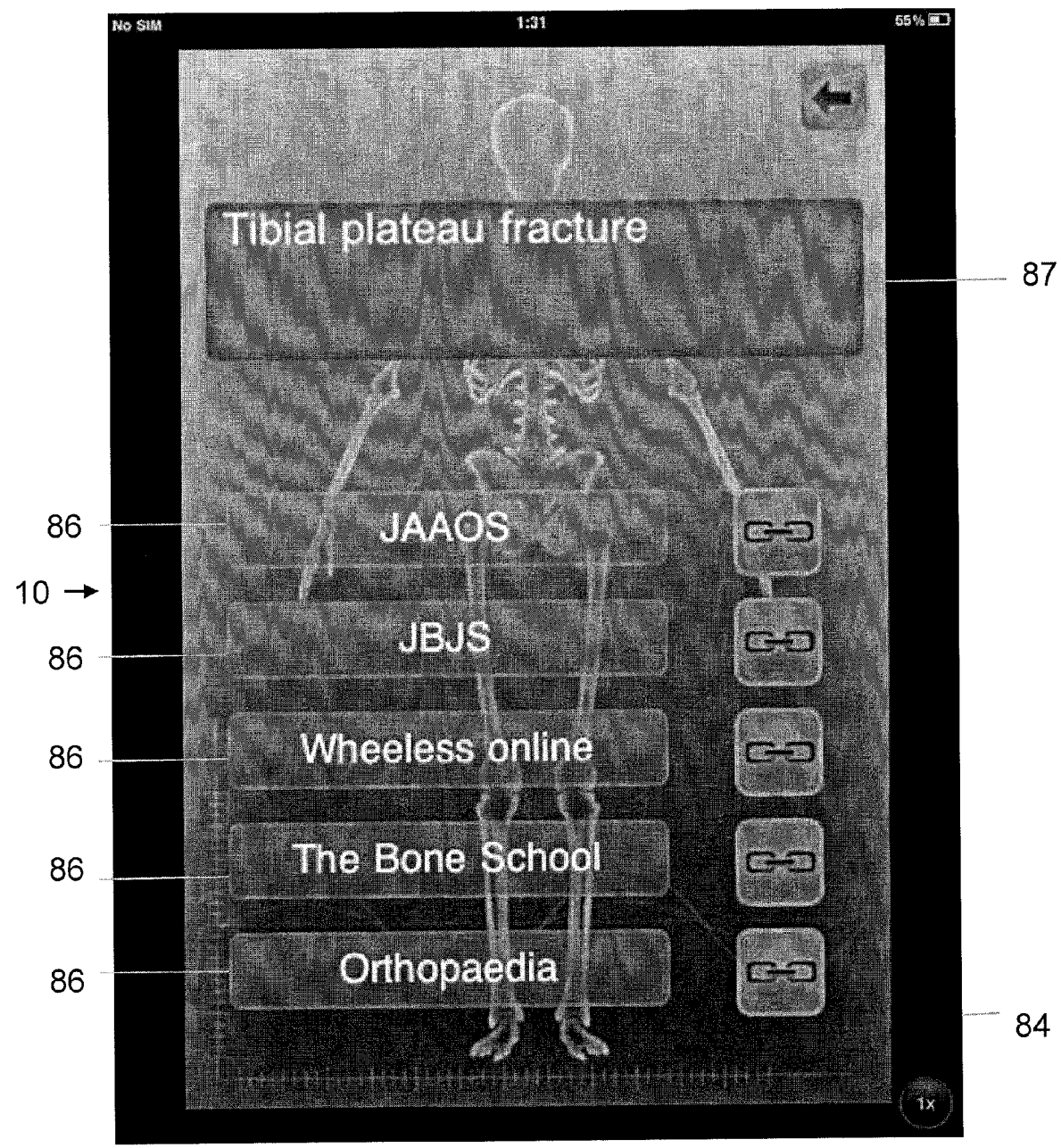
FIG. 9 shows a screenshot of the user interface showing a plurality of fields, each field containing a link to a resource containing material related to the identified abnormality.

If the user wishes to obtain further information regarding the fracture, the user activates the Search field 74. This results in the display of a screen, a screenshot 84 of which is shown in FIG. 9 of the drawings. The screen contains a number of links 86 to reference works relating to the type of fracture as displayed in a field 87. These links 86 link the user to various databases containing information of interest to the user. The links 86 make use of the diagnostic phrase or term of interest displayed in the field 87 to perform a search of the reference works, including reference works previously stored in the apparatus itself. It may be that some of these links are subscriber-only links where one needs to be a subscriber in order to access the relevant link 86.

Generally, the information accessed by a link 86 would be stored at a location remote from the device containing the user interface 10. The user accesses the relevant database in the appropriate manner, for example, via the Internet.

Figure 10:
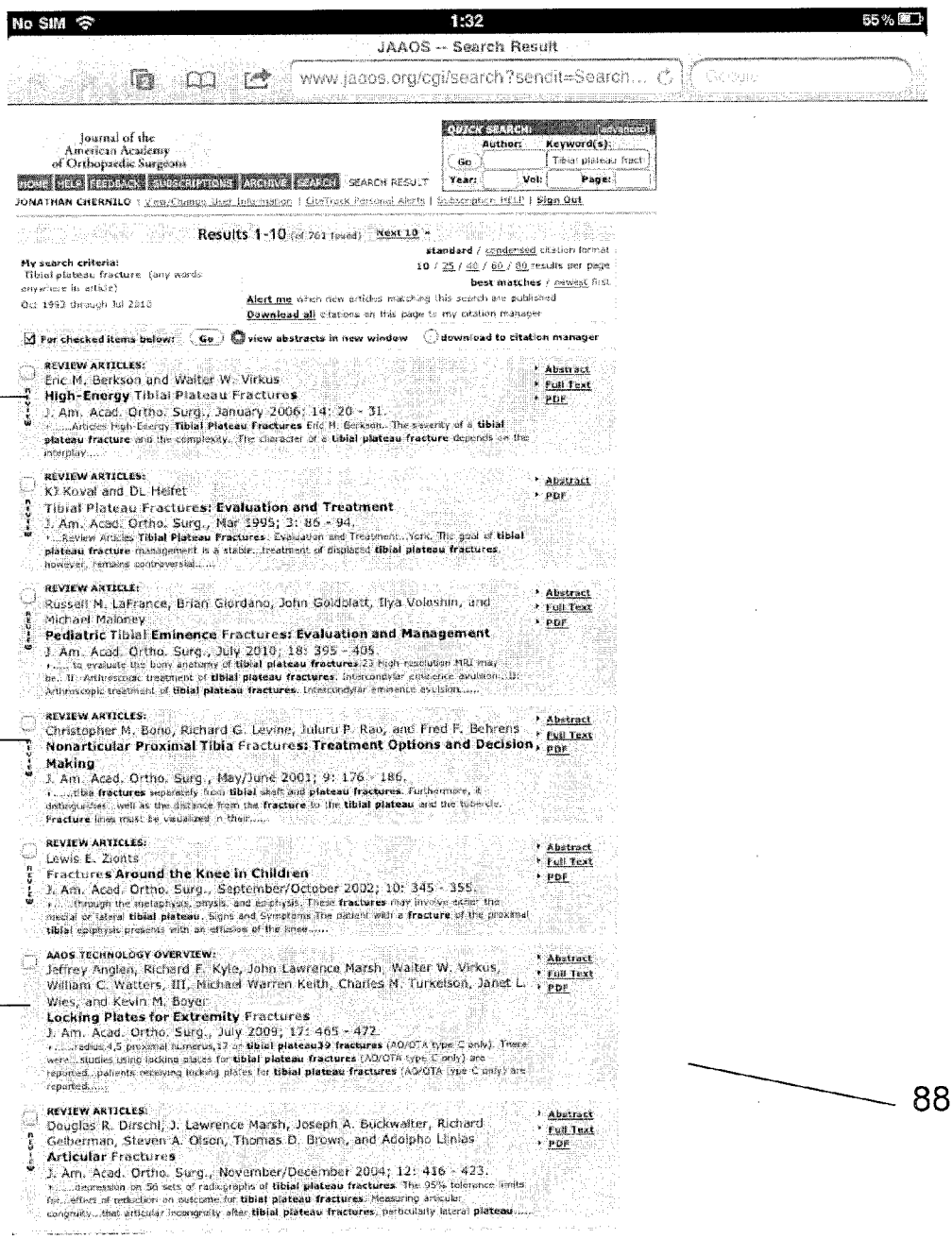
FIG. 10 shows a screenshot of the user interface showing examples of summaries of articles related to that abnormality obtained by clicking on one of the displayed links in the preceding screenshot.

Assuming the user has activated the first link 86, a further screen is displayed, a screenshot 88 of which is shown in FIG. 10 of the drawings. As illustrated in the screenshot 88, links 90 to various articles relating to the type of fracture in question as gathered by the organisation in control of that link are displayed. The user can click on one of the links 90 to gain access to the full article. As described above, this may, in certain circumstances, only be possible if the user is a subscriber to the journal or organisation in question.

Figure 11:
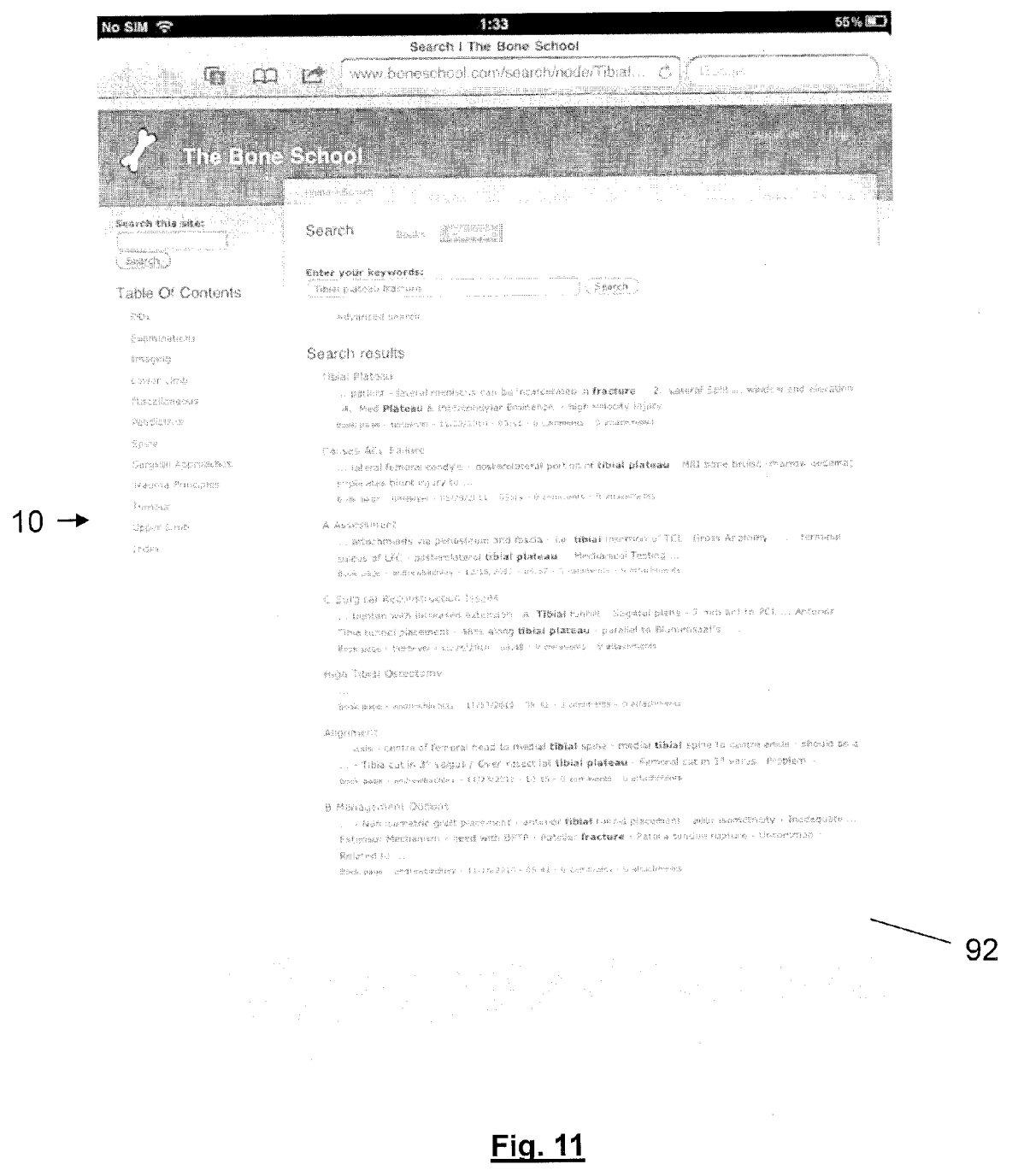

FIG. 11 shows a screenshot 92 of a further source of information which is obtained by clicking the appropriate link 86 of the screen illustrated in the screenshot 84 of FIG. 9.

Figure 12:
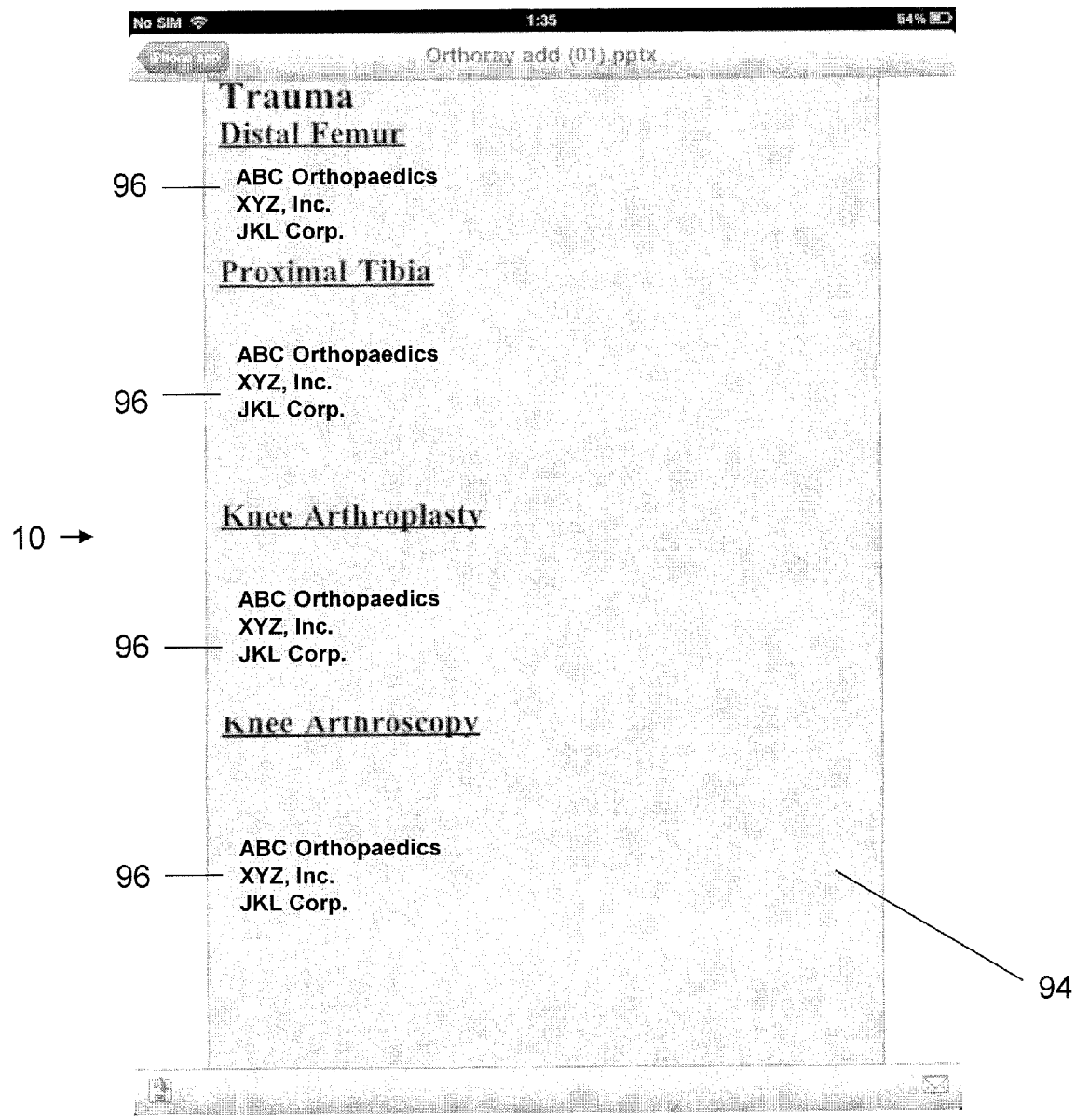
FIG. 12 shows a screenshot of the user interface showing an implant atlas containing a listing of companies that make medical devices for use in treating the identified abnormality.

If the user activates the "Implant Atlas" field 77 in the screen shown in the screenshot 70 of FIG. 7 of the drawings, a screen is displayed, a screenshot 94 of which is shown in FIG. 12 of the drawings. The screen displays a listing of companies 96 which are active in the field of medical devices relevant to the treatment of the fracture in question. These company names 96 may, themselves, be in the form of links.

Thus, the user can click on the name of the relevant company to see what medical devices that company has available for the treatment of the fracture.

If desired, the Implant Atlas" field 77 could also be used by the user to determine if the medical institution in which the user is located has the relevant medical devices in store to enable the fracture to be treated.

Figure 13:
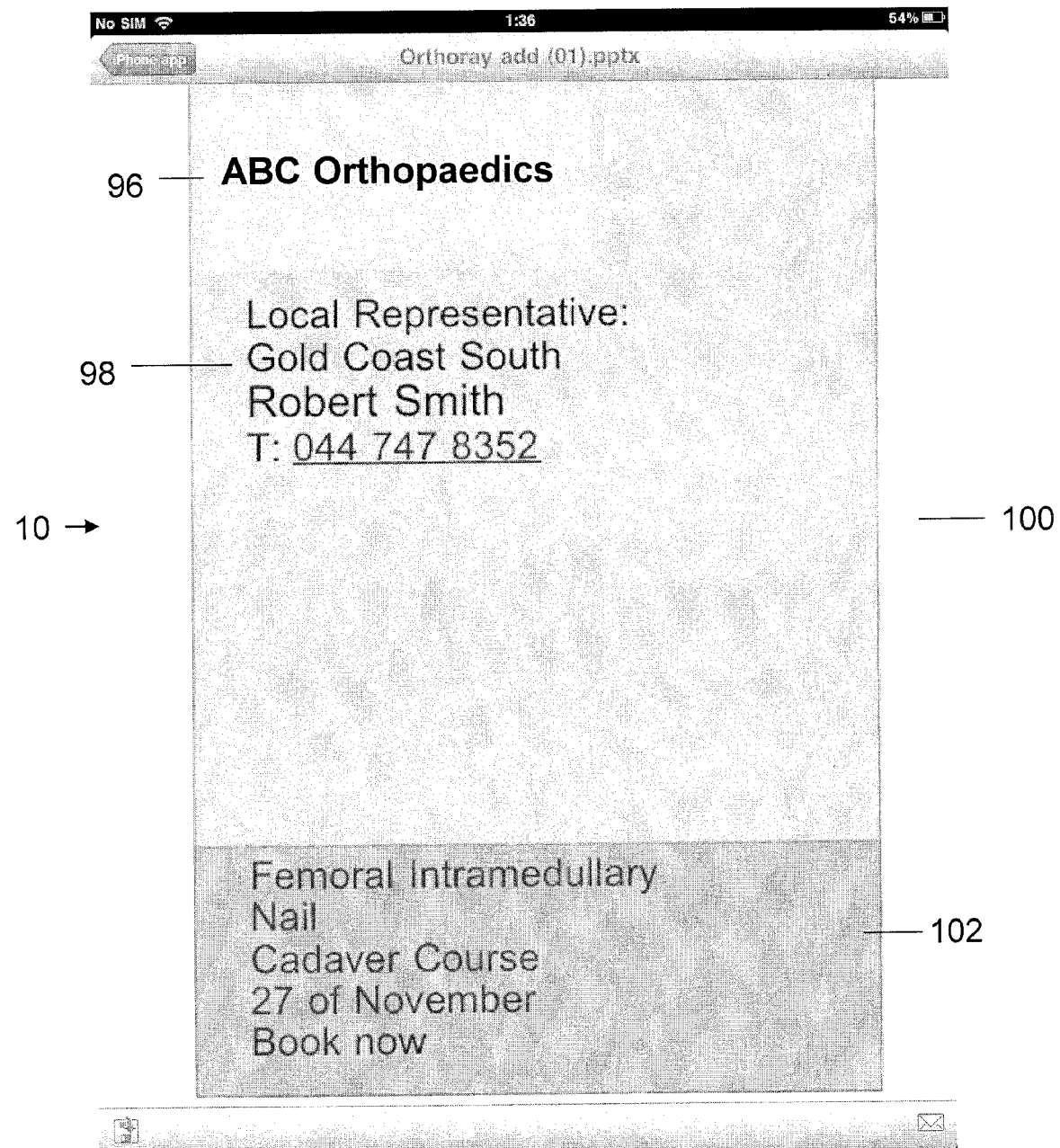
FIG. 13 shows a screenshot of the user interface showing contact details of a representative of a selected company obtained using geographical location functionality of an apparatus in which an embodiment of a computer executable medical diagnosis application, with which the user interface is associated, is installed.

The device containing the user interface 10 may have geographical location determining functionality. The user interface 10 makes use of this functionality for use with the Implant Atlas field 77. Thus, when the user clicks on the name of one of the companies 96, the user interface 10 determines the geographical location of the device and displays a screen giving the name of the local sales representative of the selected company 96 as shown at 98 in a screenshot 100 in FIG. 13 of the drawings. Further, as shown in the screenshot 100, a banner 102 can be displayed giving details of educational seminars which are available. In addition to such educational seminars, the banner 102 could contain advertising material, for example, by any of the companies 96 listed in the screenshot 94. It will be appreciated that such banners 102 could be displayed in any of the other screens as well. The banners 102 may, if desired, be linked to the diagnosis as displayed to provide treatment specific advertisements.

The user interface 10, as described above, is part of a computer executable medical diagnosis application. The application is intended to be executed on a device of the type described above, such as a mobile telephone, tablet computer, PDA, or the like. It is becoming increasingly popular that such applications are loaded into the device by purchasing the application from an on-line store or other on-line source. It is intended that this user interface 10 be loaded on to the device in a similar manner. It will, however, be appreciated that the application itself could be stored on any other suitable medium such as a memory card, USB memory stick, a computer disc, or the like.

Figure 14A:
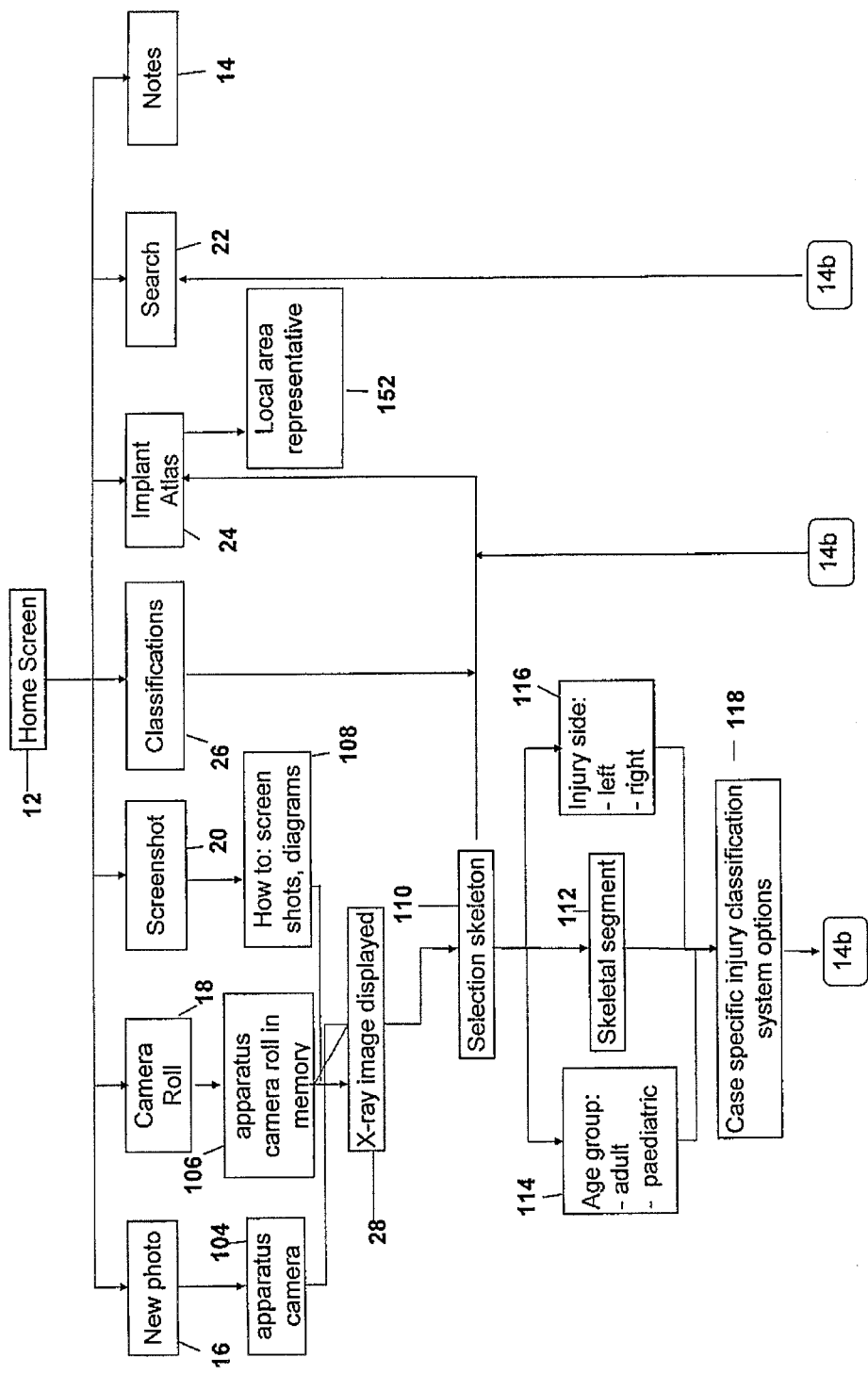
Figure 14C:
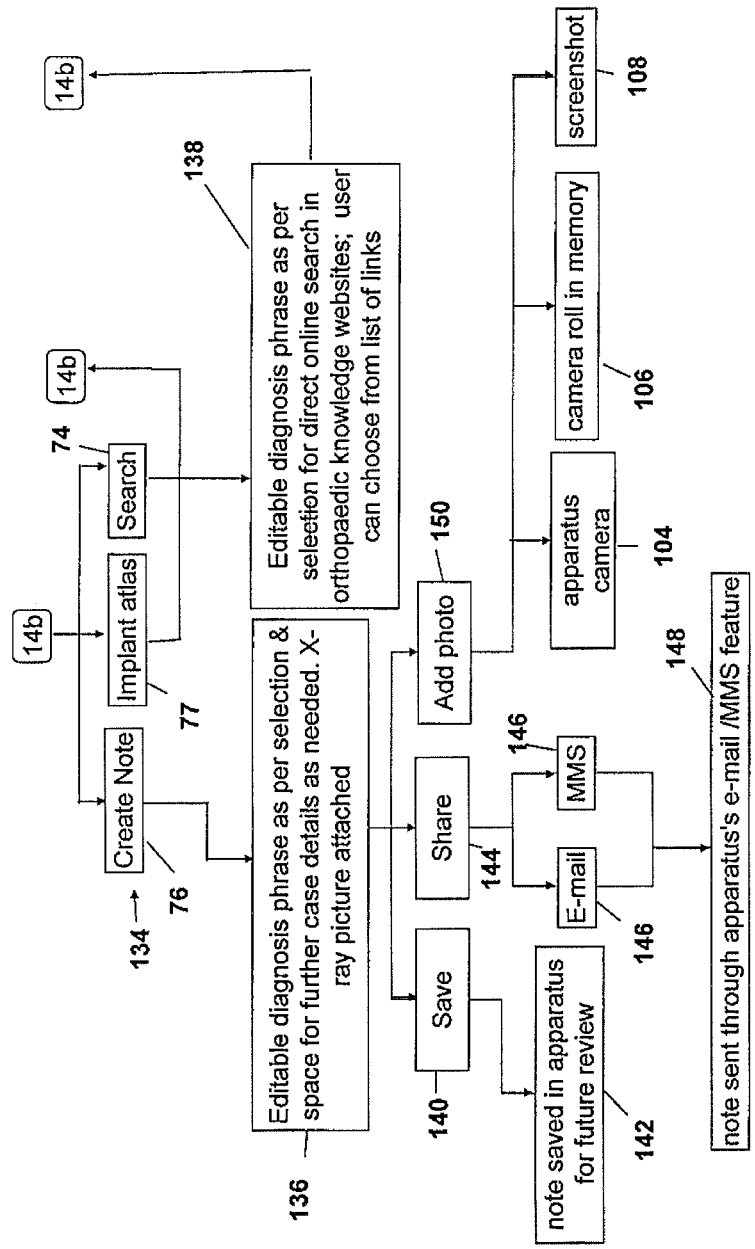

Referring now to FIGS. 14*a*-14*c* of the drawings, the operation of the application is briefly discussed.

As shown, initially, a home screen 12 is displayed. The home screen 12, as described above, displays the fields 16-26. If the New Photo field 16 is activated, a camera of the computing apparatus is used, as shown at step 104, to acquire the X-ray image 28. Instead, if the Camera Roll field 18 is activated, a memory of the apparatus is accessed to obtain the X-ray image 28 as shown at step 106. Finally, if the Screenshot field 20 is activated, functionality of the apparatus is used to obtain a screenshot of material displayed on the screen to acquire the X-ray image 28 as shown at step 108. Step 108 may also be used to explain to a user how to obtain a screenshot.

After acquisition of the X-ray image 28 occurs, the skeletal image 32 and part 34 of the skeleton 32 is displayed as shown at step 110. At step 112, the relevant skeletal segment 36 is selected, at step 114 the age group of the patient is selected and at step 116 the injury side of the patient is selected using the fields 44 and 42, respectively.

At step 118, the classification systems 48 and 50 are displayed as shown in the screenshot 46 (FIG. 3). At step 120, the user selects the appropriate classification system which results in the illustrations 50 to 58 being displayed at step 122. If the user activates the Description field 62, a written explanation of the classification system is provided at step 124.

Step 126 relates to the selection of the relevant illustration and this is followed at step 128 by the user manipulating the selected illustration 52 so that it overlies the fracture in the X-ray image 28, as described above. Once the manipulation step 128 has been completed, a diagnosis of the relevant fracture and, as shown at step 132, this causes the classification of the fracture to be displayed.

Step 134 provides the user with the relevant options to search, add a note or to access the Implant Atlas using the fields 74, 76 and 77, respectively. When the field 76 is activated, step 136 allows the user to enter a note containing details regarding the fracture, patient, etc. When the Search field 74 is activated, step 138 links this to the Search field 22 to enable the user to search resources for information relating to the fracture and/or the treatment of the fracture.

If the user has made a note regarding the fracture, the user has the option of saving the note, as shown at step 140, into the memory of the apparatus as shown as step 142. Instead, as shown at step 144, the user can use email or MMS functionality of the apparatus as shown at step 146 to send the note to third parties as shown at step 148. The user also has the option to add a photo of the X-ray image 28 as shown at step 150 using steps 104, 106 or 108 described above.

When the user accesses the Implant Atlas at step 134, the user is able to get the names of companies which make medical devices which are able to be used in fixing fractures of the type in question. Further, as shown at step 152 (FIG. 14*a*), the user can, using geographical location determining functionality of the apparatus containing the application, such as a GPS of the apparatus, obtain details of a local sales representative of the company selected. When accessing the company, the user is also able to obtain details of the types and specifications of the medical products offered by that company.

Hence, it is a particular advantage of the disclosure that a user interface 10 and its associated application are provided which enable users to obtain classification of abnormalities associated with parts of a patient's body easily and rapidly and to share this information with colleagues and third parties. This is particularly advantageous in areas which may not have ready access to major medical institutions, such as in more remote areas of a country. Users in such remote areas can forward the information to colleagues in larger regions to obtain assistance in diagnosing and treating such abnormalities.

It is another advantage of the disclosure that, by having access to resources relating to the abnormalities, users can improve their knowledge in a rapid, cost-effective manner. Still further, by being able to access details of companies which make medical devices for use in treatment of such abnormalities, the user can readily obtain the relevant medical devices and it may be possible for medical institutions to have less inventory stored on site with the resultant cost savings. A further benefit of being able to access data relating to the medical devices is that users could made aware of newer, more efficient medical devices which are available. A similar thing applies in that, by accessing the resources relating to the treatment of such abnormalities, the user may be made aware of newer and improved treatments of which the user may not have been previously aware.

It will be appreciated by persons skilled in the art that numerous variations and/or modifications may be made to the disclosure as shown in the specific embodiments without departing from the scope of the disclosure as broadly described. The present embodiments are, therefore, to be considered in all respects as illustrative and not restrictive.

The invention claimed is:

1. A user interface, configured to be installed in a computing apparatus, for medical diagnosis, the user interface including:

a display arrangement for displaying an image of a part of a patient's body on a display device of the apparatus, the part of the patient's body displayed in the image including an abnormality in the form of a physiological defect in that part of the patient's body;

a library of representations of multiple, different, physiological abnormalities associated with that part of the body, the library of representations being accessible by a user, at least some of the representations being displayed simultaneously on the display arrangement; and a selector configured to be operated by the user to select one of the representations of physiological abnormalities and to overlie the selected representation from the library on the image in the display arrangement to assist the user in identifying the physiological abnormality of that part of the patient's body.

2. The user interface of claim 1 in which the computing apparatus is a mobile apparatus.

3. The user interface of claim 1 which is configured to use an image capture device of the apparatus for capturing the image of the part of the patient's body to be displayed on the display device.

4. The user interface of claim 1 which is configured to use a memory module of the apparatus for storing data relating to the image, the data being able to be retrieved on command from the memory module to display the image on the display device.

5. The user interface of claim 1 which includes manipulation functionality for enabling the user to manipulate the selected representation to assist in identifying the abnormality.

6. The user interface of claim 5 in which the manipulation functionality comprises touch responsiveness of the display device of the apparatus to facilitate carrying out of operations by the user.

7. The user interface of claim 6 in which the operations which are able to be carried out by the user include entering notes relating to the abnormality, accessing reference works relating to the identification of the abnormality or accessing literature relating to the abnormality and/or the treatment of such abnormality.

8. The user interface of claim 7 which the operations further include adjusting the colour and/or transparency of the representation using functionality of the apparatus as per the preference of the user and to assist in identification of the abnormality.

9. The user interface of claim 7 in which the reference works and literature are subscriber-based requiring the user to be a subscriber to be able to gain access to the reference works.

10. The user interface of claim 7 in which one of the operations which is able to be carried out by the user includes accessing information relating to medical devices to be used in treating the identified abnormality.

11. The user interface of claim 10 which is configured to use geographical location determining functionality of the apparatus to enable the user to locate at least one vendor of the medical devices in, or in the vicinity of, a geographical area in which the user is located.

12. The user interface of claim 10 which is configured to use the geographical location determining functionality of the apparatus to give information about medical devices available for that abnormality and which are located in the geographical area in which the apparatus is located.

13. A user interface, configured to be installed in a computing apparatus, for medical diagnosis, the user interface including:

a display arrangement for displaying an image of a part of a patient's body on a display device of the apparatus, the part of the patient's body displayed in the image including an abnormality in the form of a physiological defect in that part of the patient's body;

a library of representations of multiple, different, physiological abnormalities associated with that part of the body, the library of representations being accessible by a user, at least some of the representations being displayed simultaneously on the display device;

a selector configured to be operated by the user to select one of the representations of physiological abnormalities and to overlie the selected representation from the library on the image in the display arrangement to assist the user in identifying the physiological abnormality of that part of the patient's body; and an accessing means for accessing a database containing information relating to medical devices available for treating the physiological abnormality.

14. The user interface of claim 13 in which the computing apparatus is a mobile apparatus.

15. The user interface of claim 13 which is configured, using the accessing means, to cooperate with geographical location determining functionality of the apparatus to enable the user to locate at least one vendor of the medical devices in, or in the vicinity of, a geographical area in which the user is located.

16. The user interface of claim 15 which is configured to use the geographical location determining functionality of the apparatus to give information about medical devices available for that abnormality and which are located in the geographical area in which the apparatus is located.

17. A non-transitory computer readable medium having a computer executable medical diagnosis application executable on a general purpose computing apparatus, the medical diagnosis application including:

a medical data input module configured to receive data relating to an image of a part of a patient's body, the image including an abnormality in the form of a physiological defect in that part of the patient's body, the medical data input module further being configured to manipulate the data to enable the image to be displayed on a display device of the computing apparatus;

a data access module for accessing a library of representations of multiple, different, physiological abnormalities associated with that part of the body, the library of representations being accessible by a user of the computing apparatus to display at least some of the representations simultaneously on the display device of the computing apparatus; and a selection module responsive to an input from the user to select one of the representations of physiological abnormalities and to enable the user to overlie the selected representation from the library on the image to assist the user in identifying the physiological abnormality of that part of the patient's body.

18. The non-transitory computer readable medium of claim 17 in which the computing apparatus is a mobile apparatus.

19. The non-transitory computer readable medium of claim 17 in which the medical data input module includes an image processing module for processing the data relating to the image for displaying the image on the display device of the computing apparatus.

20. The non-transitory computer readable medium of claim 17 in which the medical data input module includes a memory access module for accessing stored data relating to the image, the data being able to be retrieved on command from the memory module to display the image on the display device.

21. The non-transitory computer readable medium of claim 17 in which the display device of the computing apparatus is touch enabled and in which the computer readable medium includes manipulation functionality responsive to touch inputs from the user for facilitating manipulation of the selected representation relative to the image displayed on the display device to assist in identifying the abnormality, the manipulation of the selected representation comprising at least one of repositioning the selected representation, resizing the selected representation and rotating the selected representation.

22. The non-transitory computer readable medium of claim 21 in which the manipulation functionality is further configured to facilitate carrying out of operations by the user on the computing apparatus.

23. The non-transitory computer readable medium of claim 22 in which the operations which are able to be carried out by the user include at least one of entering notes relating to the abnormality, accessing reference works relating to the identification of the abnormality and accessing literature relating to the abnormality and/or the treatment of such abnormality.

24. The non-transitory computer readable medium of claim 17 in which the data access module is configured to access information relating to medical devices to be used in treating the identified abnormality.

25. The non-transitory computer readable medium of claim 24 in which the computing apparatus includes geographical location determining functionality to identify a geographical area in which the computing apparatus is located and in which the data access module is configured to locate at least one vendor of the medical devices in, or in the vicinity of, the geographical area of the computing apparatus.

26. The non-transitory computer readable medium of claim 25 in which the data access module is configured to use the functionality of the apparatus to give information about medical devices available for that abnormality and which are located in the geographical area in which the apparatus is located.

27. A non-transitory computer readable medium having a computer executable medical diagnosis application executable on a general purpose computing apparatus, the medical diagnosis application including:
a medical data input module configured to receive data relating to an image of a part of a patient's body, the part of the patient's body in the image including an abnormality in the form of a physiological defect in the part of the patient's body, the medical data input module further being configured to manipulate the data to enable the image to be displayed on a display device of the computing apparatus;
a data access module for accessing a library of representations of multiple, different, physiological abnormalities associated with that part of the body, the library of representations being accessible by a user of the computing apparatus to display at least some of the representations simultaneously on the display device of the computing apparatus; and
a selection module responsive to an input from the user to select one of the representations of abnormalities and to enable the user to overlie the selected representation from the library on the image to assist the user in identifying the physiological abnormality of that part of the patient's body;
wherein the data access module is further configured to access a database containing information relating to medical devices available for treating the abnormality.

28. The non-transitory computer readable medium of claim 27 in which the computing apparatus is a mobile apparatus.

29. The non-transitory computer readable medium of claim 27 in which the computing apparatus includes geographical location determining functionality to identify a geographical area in which the computing apparatus is located and in which the data access module is configured to locate at least one vendor of the medical devices in, or in the vicinity of, the geographical area of the computing apparatus.

30. The non-transitory computer readable medium of claim 29 in which the data access module is configured to use the functionality of the apparatus to give information about medical devices available for that abnormality and which are located in the geographical area in which the apparatus is located.

31. A computer implemented method for medical diagnosis to be executed on a general purpose computing apparatus, the method including:
receiving data relating to an image of a part of a patient's body including an abnormality in the front of a physiological defect and manipulating the data to enable the image to be displayed on a display device of the computing apparatus;
accessing a library of representations of multiple, different, physiological abnormalities associated with that part of the body and displaying at least some of the representations simultaneously on the display device of the computing apparatus; and
selecting one of the representations of physiological abnormalities and overlying the selected representation from the library on the image to assist the user in identifying the physiological abnormality of that part of the patient's body.

32. The method of claim 31 which includes accessing information relating to medical devices to be used in treating the identified abnormality.

33. The method of claim 32 which includes identifying a geographical area in which the computing apparatus is located and locating at least one vendor of the medical devices in, or in the vicinity of, the geographical area of the computing apparatus.

34. The method of claim 33 which includes giving information about medical devices available for that abnormality and which are located in the geographical area in which the apparatus is located.

35. The method of claim 31 which includes processing the data relating to the image for displaying the image on the display device of the computing apparatus.

36. The method of claim 31 which includes accessing stored data relating to the image, the data being able to be retrieved on command from the memory module to display the image on the display device.

37. The method of claim 31 in which the display device of the computing apparatus is touch enabled and includes manipulation functionality responsive to touch inputs from the user and in which the method includes using the manipulation functionality to manipulate the selected representation relative to the image displayed on the display device to assist in identifying the abnormality, the manipulation of the selected representation comprising at least one of repositioning the selected representation, resizing the selected representation and rotating the selected representation.

38. The method of claim 37 which includes using the manipulation functionality to carry out operations by the user on the computing apparatus, the operations to be carried out by the user including at least one of entering notes relating to the abnormality, accessing reference works relating to the identification of the abnormality, and accessing literature relating to the abnormality and/or the treatment of such abnormality.

39. A computer implemented method for medical diagnosis to be executed on a general purpose computing apparatus, the method including:

receiving data relating to an image of a part of a patient's body including an abnormality in the form of a physiological defect and manipulating the data to enable the image to be displayed on a display device of the computing apparatus;

accessing a library of representations of multiple, different, physiological abnormalities associated with that part of the body and displaying at least some of the representations simultaneously on the display device of the computing apparatus;

selecting one of the representations and overlying the selected representation from the library on the image to assist the user in identifying the physiological abnormality of that part of the patient's body; and accessing a database containing information relating to medical devices available for treating the abnormality.

40. The method of claim 39 which includes identifying a geographical area in which the computing apparatus is located and locating at least one vendor of the medical devices in, or in the vicinity of, the geographical area of the computing apparatus.

41. The method of claim 40 which includes giving information about medical devices available for that abnormality and which are located in the geographical area in which the apparatus is located.

42. A handheld device including a user interface as claimed in claim 1.

43. The handheld device of claim 42 which is a mobile device.

44. The handheld device of claim 42 in which the user interface is generated from a computer executable medical diagnosis application carried by a computer readable medium as claimed in claim 17.

45. The handheld device of claim 42 in which the user interface is generated from a computer executable medical diagnosis application carried by a computer readable medium as claimed in claim 27.

* * * * *